United States Patent
Wong et al.

(10) Patent No.: US 7,972,621 B2
(45) Date of Patent: Jul. 5, 2011

(54) PROCESS FOR FORMULATING FAST DISPERSING DOSAGE FORMS COMPRISING AT LEAST ONE FISH GELATIN SELECTED ON THE BASIS OF MOLECULAR WEIGHT

(75) Inventors: Desmond Yik Teng Wong, Wootton Bassett (GB); Leon Paul Grother, Swindon (GB); Andrzej Jan Brzozowski, Swindon (GB)

(73) Assignee: R.P. Scherer Technologies, LLC, Carson City, NV (US)

( * ) Notice: Subject to any disclaimer, the term of this patent is extended or adjusted under 35 U.S.C. 154(b) by 1107 days.

(21) Appl. No.: 10/860,106

(22) Filed: Jun. 3, 2004

(65) Prior Publication Data

US 2005/0271719 A1 Dec. 8, 2005

(51) Int. Cl.
*A61K 9/20* (2006.01)
*A61K 9/48* (2006.01)
*A61K 9/64* (2006.01)

(52) U.S. Cl. ........ 424/464; 424/451; 424/452; 424/456; 424/465

(58) Field of Classification Search ........................ None
See application file for complete search history.

(56) References Cited

U.S. PATENT DOCUMENTS

| | | | | |
|---|---|---|---|---|
| 4,760,093 A | 7/1988 | Blank et al. | .................... | 514/629 |
| 4,760,094 A | 7/1988 | Blank et al. | .................... | 514/629 |
| 4,767,789 A | 8/1988 | Blank et al. | .................... | 514/629 |
| 5,039,540 A | 8/1991 | Ecanow | ........................ | 426/385 |
| 5,079,018 A | 1/1992 | Ecanow | ........................ | 426/385 |
| 5,330,763 A | 7/1994 | Gole et al. | ..................... | 424/484 |
| 6,110,486 A | 8/2000 | Dugger, III | .................... | 424/435 |
| 6,258,380 B1 | 7/2001 | Overholt | ........................ | 424/456 |
| 6,284,270 B1 | 9/2001 | Lagoviyer et al. | | |
| 6,465,010 B1 | 10/2002 | Lagoviyer et al. | | |
| 6,709,669 B1 * | 3/2004 | Murray et al. | ................. | 424/434 |
| 6,726,928 B2 | 4/2004 | Yarwood et al. | ............... | 424/464 |
| 2004/0076666 A1 | 4/2004 | Green et al. | | |
| 2004/0138098 A1 | 7/2004 | Fein | | |
| 2005/0232997 A1 | 10/2005 | Nilsson et al. | | |
| 2006/0134194 A1 | 6/2006 | Banbury et al. | | |
| 2008/0274951 A1 | 11/2008 | Fein | | |
| 2009/0005432 A1 | 1/2009 | Fein | | |
| 2009/0318665 A1 | 12/2009 | Nilsson et al. | | |
| 2010/0056436 A1 | 3/2010 | Fein | | |

FOREIGN PATENT DOCUMENTS

| | | | |
|---|---|---|---|
| EP | 1 367 066 A2 | * | 12/2003 |
| GB | 1548022 | | 7/1979 |
| GB | 2111423 | | 6/1983 |
| IL | 145783 | | 10/2006 |
| WO | WO94/11438 | | 5/1994 |
| WO | WO94/14422 | | 7/1994 |
| WO | 00/61117 A1 | | 10/2000 |
| WO | 01/10418 A1 | | 2/2001 |
| WO | 2004/041153 A2 | | 5/2004 |
| WO | 2004/043439 A1 | | 5/2004 |

OTHER PUBLICATIONS

EP Pharmacopoeia 4$^{th}$ ed. Section 2.6.12 (Microbial Examination of Non-Sterile Products (Total Viable Aerobic Count)].
Supplementary European Search Report dated Feb. 7, 2011 issued in European Appln. No. 05758824.6.

* cited by examiner

*Primary Examiner* — Humera Sheikh
(74) *Attorney, Agent, or Firm* — Fitzpatrick, Cella, Harper & Scinto

(57) ABSTRACT

The invention disclosed herein relates to a pharmaceutical composition comprising a carrier and an active ingredient, wherein the carrier is at least one fish gelatin predetermined on the basis of the molecular weight profile of the gelatin. In some embodiments, particularly when the concentration of carrier comprises a relatively lower percentage of the total composition, the carrier may be exclusively a high molecular weight fish gelatin, or may be comprised of a mixture with standard molecular weight gelatin in which high molecular weight gelatin comprises a predominant portion. In those embodiments where the concentration of carrier comprises a relatively larger percentage of the total composition, the carrier may be an exclusively standard molecular weight fish gelatin, or may be comprised of a mixture in which standard molecular weight gelatin comprises a predominant portion. Thus, compositions may be designed to optimize performance for various required gelatin concentration formulations.

33 Claims, No Drawings

PROCESS FOR FORMULATING FAST DISPERSING DOSAGE FORMS COMPRISING AT LEAST ONE FISH GELATIN SELECTED ON THE BASIS OF MOLECULAR WEIGHT

TECHNICAL FIELD

The instant invention relates to pharmaceutical preparations comprising a fast dispersing dosage form, particularly, to a freeze-dried fast dispersing dosage form comprising high and standard molecular weight fish gelatins and combinations thereof.

BACKGROUND OF THE INVENTION

A common route for the administration of pharmacologically active agents is a plurality of oral dosage forms; including such familiar forms as tablets, pills, and capsules. Such dosage forms are generally convenient, stable in storage and transport, and familiar to the user. However, they are not without problems, and these problems are often significant. It is extremely difficult for most people to swallow any of these oral dosage forms without supplemental water. In the fast-paced world, it is frequently inconvenient or messy to have to take supplementary water with oral medicaments. Such difficulties are compounded for those with difficulty in swallowing, such as, for example, children and the elderly. Certain medical conditions, such as Parkinsonism or other neurological states, make it difficult to swallow oral dosage forms, even with supplemental water.

The need for supplementary water may be obviated by dispensing liquid medicaments. However, these are messy, as well as difficult to transport and dose properly. Accordingly, efforts have been directed to combining the best features of dry medicaments, for example, tablets, pills, or capsules, such as their ease of transport, accurate dosing, and robust product forms with the best features of liquid medications, such as their ability to be taken without supplemental water and by those with difficulty in swallowing.

Additionally, swallowing oral dosage forms intact implicates a complex system of variables involved in gastrointestinal dissolution of dosage forms and absorption of drugs.

Accordingly, there is considerable interest in oral medicaments and so-called "pre-gastric absorption" of active ingredients. Pre-gastric absorption is the absorption of active ingredients from that part of the alimentary canal prior to the stomach. Pre-gastric absorption thus includes buccal, sublingual, oropharyngeal and esophageal absorption. Medicaments absorbed by such pre-gastric absorption pass straight into the systemic circulatory system, thereby avoiding first pass metabolism in the liver. Accordingly, bioavailability of agents absorbed in this way may also be increased. This means that the dose of such agents may be reduced while still producing the desired beneficial effects, and this decrease in dose may result in a corresponding reduction of unwanted side effects. Current research, as noted in U.S. Pat. No. 6,110,486 to Dugger, shows in particular that absorption through the buccal mucosa represents an often underappreciated route of oral administration that is unavailable to drugs in tablet, pill, or capsule form.

One direction in these efforts has been the development of oral solid pharmaceutical dosage forms that rapidly disintegrate in the mouth. These materials are typically denominated fast dispersing dosage forms. An example is seen in U.S. Pat. No. 5,079,018 to Ecanow, that discloses a fast dispersing dosage form which comprises a porous skeletal structure of a water soluble, hydratable gel or foam forming material which has been hydrated with water. The gel or foam forming material is rigidified in the hydrated state with a rigidifying agent and dehydrated with a liquid organic solvent at a temperature of about 0 degrees C. or below to leave spaces in place of the hydration liquid. Oral solid pharmaceutical dosage forms which rapidly disintegrate in the mouth and methods for their preparation have been proposed in GB A-1548022 and GB-A-2111423. The solid dosage forms as disclosed comprise an open matrix network carrying the pharmaceutically active substance, with the open matrix comprising a water-soluble or water-dispersible carrier material that is inert towards the pharmaceutically active substance. The solid dosage forms are prepared by the sublimation or removal of solvent from a solution or suspension comprising the pharmaceutically active substance and the carrier material. Sublimation or removal of solvent is preferably carried out by freeze-drying, or lyophilization. A typical approach is to dose a drug solution or suspension into free form blisters followed by rapidly freezing the solution or suspension and then freeze-drying. Freeze-drying removes the ice to leave a porous tablet that, when placed on the tongue, disperses in a few seconds. The drug is then swallowed with the saliva. Other methods for preparing oral solid pharmaceutical forms which rapidly disintegrate in the mouth are disclosed in U.S. Pat. Nos. 5,039,540; 5,120,549; and 5,330,763, as well as PCT/JP93/01631 and PCT/U.S.93/12566. Other relevant patents in this technology are U.S. Pat. Nos. 4,760,093; 4,760,094; and 4,767,789.

As seen in the prior art, a typical matrix forming agent is gelatin. Typically, gelatin is used to give sufficient strength to the dosage form to prevent breakage during removal from packaging, but once placed in the mouth, the gelatin allows immediate dispersion of the dosage form. Gelatin, which is normally utilized in such formulations, is defined as a protein obtained by partial hydrolysis of mammalian collagenous tissues, such as skins, tendons, ligaments and bones. Gelatin may also be derived from fish. In comparing gelatin sources, the required heating step of processing mammalian gelatin increases processing time and costs, thereby increasing the overall costs of the process, compared to that for fish gelatin. Additionally, various cultural and religious factors, along with perceptions of health risk in bovine and porcine products, may make fish gelatin more attractive than mammalian gelatin to consumers.

Particularly for pharmaceutical formulations, an advantageous alternative to the use of mammalian derived gelatin is the use of fish gelatin, especially non-gelling fish gelatin. Non-gelling fish gelatin is preferably obtained from cold water fish and has a sol-gel transition temperature, that is, the temperature at which a given solution of gelatin in water, transitions between a liquid and a gel state, that is lower than that of most mammalian derived gelatins. There appears to be a relationship between the temperature at which the animal or fish metabolizes food and the properties of the skin and resultant extracted gelatins.

U.S. Pat. No. 6,709,669 ('669) to Murray teaches the use of a fish gelatin based carrier and an active ingredient, designed for oral and topical dosage forms, as well as a method for lyophilizing, or freeze-drying, and packaging a combination of the active ingredient and the fish gelatin. In a preferred embodiment disclosed in the '669 patent, the composition of the invention is a solid fast-dispersing dosage form containing a network of the active ingredient and a water soluble or water-dispersible carrier comprising fish gelatin (e.g., non-gelling fish gelatin), the network having been formed by subliming solvent from a composition in the solid state containing the active ingredient and a solution or dispersion of the carrier in a solvent.

However, the previous invention of the '669 dosage forms used a commercially available grade of fish gelatin with a molecular weight profile defined by the supplier (Croda Colloids, Ltd.; Cheshire, England). However, gelatin is a naturally occurring, non-homogenous entity, capable of significant variation in chemistry and therefore, considerable variation in physical properties. By way of example and not limitation, experimentation has shown that using a formulation containing certain concentrations of certain grades of fish gelatin, it may not be possible to produce products with a desirable physical robustness and surface appearance. Accordingly, a means has been sought to devise manufacturing methods for fish gelatin products, particularly fast dispersing dosage forms, driven by a quantifiable measurement of at least one chemical property of the gelatin. Ideally, such measurable parameters would improve the ability to prospectively and empirically design a manufacturing protocol with a high degree of commercially effective reproducibility.

SUMMARY OF THE INVENTION

It is now well know that many of the problems associated with the use of mammalian gelatin can be overcome if fish gelatin, especially non-gelling or so-called "cold water" fish gelatin, is utilized for preparing fast-dispersing dosage forms.

In its most general configuration, the present invention advances the state of the art with a variety of new capabilities and overcomes many of the shortcomings of prior dosage forms in new and novel ways.

In one of the simplest configurations, the instant invention provides a process for formulating a pharmaceutical composition comprising a carrier and an active ingredient (e.g., drug, compound, and the like) wherein the carrier is at least one fish gelatin, selected at least in part on the basis of molecular weight, and the composition is in the form of a fast dispersing dosage form which releases the active ingredient rapidly on contact with a fluid (e.g., saliva, bodily fluids, water, and the like).

In various embodiments, different fish gelatins, selected at least in part on the basis of molecular weight, are selected to optimize compositional performance. A preferred combination of at least two fish gelatins of differing molecular weight profiles is shown to improve the compositional performance of various fast dispersing dosage forms across an enhanced range of formulations.

This, then, is disclosed: A process for preparing a pharmaceutical composition having a predetermined final total gelatin concentration in a fast dispersing dosage form containing at least one active ingredient and at least one carrier inert to the active ingredient selected from the group consisting of high molecular weight fish gelatin, standard molecular weight fish gelatin, and combinations thereof. The steps of the process include selecting the at least one carrier based at least in part on the molecular weight profile of the carrier and the intended predetermined final total gelatin concentration of the composition and forming a mixture of the at least one active ingredient and at least one carrier in a suitable solvent to create a formulation. The formulation may exhibit a fairly constant viscosity over a period of about 48 hours.

The formulation is then dosed into discrete units; the discrete units are solidified; and solvent is removed from the solid discrete units to form a network of the at least one active ingredient and at least one carrier. The process may result in a predetermined final total gelatin concentration of between 2% and 7% w/w of the final formulation. The fish gelatin may be a non-gelling fish gelatin and may be a non-hydrolyzed fish gelatin, and the solvent in some embodiments is water. Solvent may be removed by freeze-drying, forced-air drying, a second solvent removal process; or by other methods well-known to those skilled in the art.

In some embodiments, the at least one fish gelatin carrier further comprises a first gelatin further comprising a high molecular weight gelatin in which more than 50%, preferably more than 60% and most preferably more than 70% of the molecular weight distribution of the gelatin is greater than 30,000 daltons. In other embodiments, the at least one fish gelatin carrier further comprises a second gelatin further comprising a standard molecular weight gelatin in which more than substantially 50%, preferably more than 60% and most preferably more than 70% of the molecular weight distribution of the gelatin is below than 30,000 daltons.

Various combinations are disclosed, including those where the combination of high molecular weight and standard molecular weight gelatin contains more than 50% high molecular weight gelatin; those where the combination of high molecular weight and standard molecular weight gelatin contains more than 50% standard molecular weight gelatin. Combinations may be formed wherein the ratio of high molecular weight gelatin to standard molecular weight gelatin (HMW:SMW) ranges substantially from 1:1 to 1:9. The solid, oral, rapidly disintegrating dosage form may also contain coloring agents, flavoring agents, excipients, and multiple therapeutic agents.

In some embodiments, the composition is designed for oral administration and releases the active ingredient rapidly in the oral cavity, which may occur in from 1 to 30 seconds, more preferably in from 1 to 20 seconds, and most preferably in from 1 to 10 seconds of being placed in fluid.

The teaching below also discloses the forms produced by the processes disclosed above.

DETAILED DESCRIPTION OF THE INVENTION

The fast dispersing dosage forms containing a single grade of fish gelatin, or combinations of fish gelatins differing in molecular weight profiles, of the instant invention enables a significant advance in the state of the art. The preferred embodiments of the dosage forms accomplish this by new and novel combinations of elements that demonstrate previously unavailable but preferred and desirable capabilities.

The phrase "rapidly dispersing dosage form," in an in vivo context, refers to dosage forms which disintegrate or disperse within 1 to 60 seconds, preferably 1 to 30 seconds, more preferably 1 to 10 seconds, and particularly 2 to 8 seconds, after being placed in contact with a fluid. The fluid is preferably that found in the oral cavity, i.e., salvia. In a general context, the phrase encompasses all the previously motioned dosage forms described herein as well as any equivalent dosage form.

The term "rapidly dispersing" as used in the experimental protocols described herein means that the solid dosage form will disperse in water at 37 degrees C. in 60 seconds or less. The forms usually disintegrate in about 5-20 seconds, more usually 5 to 10 seconds or less.

The following protocol was used to test and measure dispersion time:

Adjust the temperature of a suitable water bath to 37° C.+/−0.5° C. Check that the water level is above the minimum fill line; if not then add water as needed. Place approximately 600 ml water into a 1000 ml beaker and place the beaker into the water bath. Once sufficient time for temperature equilibration to occur has passed, the temperature of the water in the beaker is checked using a calibrated thermometer and recorded. When the correct temperature has been reached, the dispersion test apparatus is ready for use.

A sample of six fast dispersing dosage forms is removed from the packaging. These units should be randomly chosen from across the batch under test. Using a pair of tweezers, a single unit of one of the chosen forms is dropped flatly onto the surface of the water in the beaker. A calibrated stopwatch is used to measure the time taken for the form to become fully wetted. This is the dispersion time in seconds. Repeat for all fast dispersing dosage forms in the chosen sample ensuring that each form is dropped onto a clear region of the water in the beaker, free from the remains of previously dispersed units. Each dispersion time for the six chosen units is recorded.

In a preferred embodiment, the compositions of the invention are solid fast-dispersing dosage forms comprising a solid network of the active ingredient and a water-soluble or water-dispersible carrier containing at least one fish gelatin. Accordingly, the carrier is inert towards the active ingredient. The network is obtained by removing solvent from a composition in the solid state, the composition comprising the active ingredient and a solution of the carrier in the solvent. The final dosage forms according to the invention can be prepared according to the process disclosed in Murray et al., U.S. Pat. No. 6,709,669 and Gregory et al., U.K. Patent No. 1,548,022, using fish gelatin as the carrier. Removal of solvent can be accomplished by various methods, including by way of example, sublimation, forced-air drying, and second solvent removal processes, such as those described in U.S. Pat. No. 6,726,928 ('928) and incorporated herein by reference.

The fast dispersing dosage forms of the instant invention were formulated according to the general plan as described below:

General Description of the Formulations

| Material | Purpose |
| --- | --- |
| Fish Gelatin (HMW) | Matrix Former |
| Fish Gelatin (SMW) | Matrix Former |
| Mannitol | Provide Unit Rigidity and Improve Appearance, Texture, and Taste |
| Sodium Hydroxide (NaOH) | pH Adjustment |
| Purified Water | Solvent (Removed During Processing) |

High molecular weight gelatin (HMW) is defined as a gelatin in which more than 50% of the molecular weight distribution is greater than 30,000 Daltons, while standard molecular weight (SMW) gelatin is defined as a gelatin in which more than 50% of the molecular weight distribution is below 30,000 Daltons.

In the instant invention, molecular weight distributions of the gelatins were determined according to the following general protocol:

The chromatographic method for the determination of molecular weight distributions of gelatin uses a TSK Gelsw (7.5×7.5 mm) guard column and two TSK gel 4000SWXL (300×7.8 mm) main columns in series. The HPLC unit is set up with the following conditions: Flow Rate: 0.5 ml/min; Wavelength: 220 nm; Injection Volume: 20 µl; Column Temperature: 25° C.; Run Time: 70 mins.; and Mobile Phase Composition: 71 g of sodium sulphate (Na2SO4), 15.6 g of sodium dihydrogen phosphate (NaH2PO4.2H2O), and 25 g of sodium dodecylsulphate (C12H25NaO4S) dissolved in 5 liters of water and pH adjusted to pH 5.3 using 1N sodium hydroxide. Polyethylene glycol and polyethylene oxide standards were used to mark 10 MW gradients from 1900 to 439600 g/mol.

The sample was prepared by dissolving 100 mg of gelatin in a 100 ml volumetric flask made up to the mark with a mixture of 90% mobile phase and 10% ethylene glycol. Any standard HPLC/GPC software package can be used to analyze the data.

General Preparation of Formulations and Fast Dispersing Dosage Forms

Hereinafter, the term "formulation" is used to describe the composition before it is dried into its final form, while the term "fast dispersing dosage form" is used to describe the final product after dosing and drying. The data reported below were generated from samples made using bench scale equipment and manufacturing processes with a batch size of 900 grams for each sample formulation. To make a pre-mix, gelatin and mannitol were added to an aliquot of purified water of not less than 50% by weight of the total predicted batch requirement in a 1 liter vessel and stirred. The pre-mix was heated to 60° C. in a water bath and stirred at 100 rpm for 1 hour. The pre-mix was then chilled to the respective dosing temperatures of the experimental protocol (5° C., 10° C., 15° C., and 23° C.; as detailed below). The pre-mix was then made up to 900 grams with purified water. A paddle stirrer speed of 100 rpm was used throughout the mixing process.

The pre-mix was stirred at 100 rpm for up to 48 hours and dosed at respective dosing temperatures (5° C., 10° C., 15° C., and 23° C.; as detailed below). The 48-hour hold time was selected to replicate commercial dosing protocols, where formulations may need to be held for extended periods to allow completion of the dosing of a commercially sized batch. The pre-mix was dosed into pre-formed blister packs using a semiautomatic pump set to dispense the appropriate fill weight, such as 250 mg wet fill weight. Once dosed, the filled blister packs were passed through a liquid nitrogen freeze tunnel using a set temperature of not warmer than −50° C. and a typical residence time of 3 minutes and 15 seconds. All frozen products were immediately placed in a refrigerated cabinet set at a temperature sufficiently cold to ensure that the dosed products were maintained frozen during storage prior to freeze-drying. The frozen products were then freeze dried using a shelf temperature of 0° C. and a chamber pressure of 0.5 mbar. The freeze dried products, that is, the fast dispersing dosage forms, were then placed in a dry storage cabinet prior to finished product evaluation.

Evaluation Methods

For each of the formulations held at the different dosing temperatures, the following assessments were made:

Dosability—The formulation was checked for signs of gelling. The ease of dosing using a semi-automatic dosing pump was visually assessed for evidence of physical blockage of the dosing tube and for the presence of air bubbles in the dosed solution. Formulations that were gelled at the end of the hold time, are not dosable, and were not tested further.

Viscosity—The viscosity of the pre-mix was monitored at regular intervals over the 48 hour hold period. Viscosity was tested using a Haake VT550 Viscotester fitted with a NV rotational sensor. The viscosity was recorded at shear rates between 500 and 2500 (1/s) with the temperature of the sensor maintained at the same temperature as the sample.

Microbiological Quality—At the relevant hold times, a sample of the formulation was taken for Total Viable Count (TVC). A count of less than 1000 cfu/ml (colony forming units/ml was deemed passing, and a count above that level was deemed failing. The TVC was determined according to the plate count method detailed in European Pharmacopoeia (4th Ed.) §2.6.12 ["Microbial Examination of Non-Sterile Products (Total Viable Aerobic Count)"]. For the purpose of the instant invention, microbiological quality was tested as an advisory parameter only, that is, no formulation was eventually deemed absolutely unsuccessful because it failed the TVC. This was decided due to the fact that experimentation was undertaken using no active ingredient in the fast dispersing dosage forms. Variations in the pH of formulations, various characteristics of an active ingredient, and various preservatives, such as, by way of illustration and not limitation, bacteriostatic and bactericidal agents, may affect the microbiological quality of an ultimately finished fast dispersing dosage form.

The quantity of an active agent will vary according to the particular drug selected and the patient's needs. However, the active agent can be generally present in an amount form about 0.01% to about 85%, typically from about 0.02% to about 60%, by weight of the composition of the dried dosage form.

Fast dispersing dosage forms were evaluated for the following:

Visual Inspection of Finished Product—surface appearance and cosmetic surface defects, sometimes including what is referred to as "nodules," and evaluated under the term "Surface Appearance," and the amount of residue present in the blister pack pocket following removal of unit.

Dispersal Time—per the protocol detailed above, with less than 10 seconds denoting fast dispersion; and greater than 20 seconds denoting slow, or unacceptable, dispersion.

Variable—means that dispersion time was less consistent, but always within an acceptable range; that is, a sample might disperse in less than 10 seconds in one experiment, but then disperse in between 10 and 20 seconds in another experiment.

As a threshold evaluation, gelatin compositions were formulated with either exclusively high molecular weight (HMW) or exclusively standard molecular weight (SMW) gelatin (Norland Products, Inc.). HMW gelatins are defined as gelatins in which more than 50% of the molecular weight distribution is greater than 30,000 Daltons. In contrast, SMW gelatins are gelatins in which more than 50% of the molecular weight distribution is below 30,000 Daltons.

TABLE 1

High and Standard Molecular Weight Formulations

| Batch Code | HMW Gelatin; % w/w | SMW Gelatin; % w/w | Mannitol % w/w | Dosing Temp. (° C.) |
|---|---|---|---|---|
| 1A | 3.5 | 0 | 2.96 | 5 |
| 1B | 3.5 | 0 | 2.96 | 23 |
| 2A | 5 | 0 | 4.23 | 5 |
| 2B | 5 | 0 | 4.23 | 23 |
| 3A | 6.5 | 0 | 5.5 | 5 |
| 3B | 6.5 | 0 | 5.5 | 23 |
| 4A | 0 | 3.5 | 2.96 | 5 |
| 4B | 0 | 3.5 | 2.96 | 23 |
| 5A | 0 | 5 | 4.23 | 5 |
| 5B | 0 | 5 | 4.23 | 23 |
| 6A | 0 | 6.5 | 5.5 | 5 |
| 6B | 0 | 6.5 | 5.5 | 23 |

TABLE 2

Evaluation Results of HMW Formulations

| Batch Code | Gelatin Concn. % | ° C. | Dosability | Viscosity | Total Viable Count | Surface Appearance | Residue | Dispersion |
|---|---|---|---|---|---|---|---|---|
| 3A | 6.5 | 5 | Gelled | * | * | * | * | * |
| 3B | 6.5 | 23 | Satisfactory | Constant | Fail | Good | No | Slow |
| 2A | 5.0 | 5 | Gelled | * | * | * | * | * |
| 2B | 5.0 | 23 | Satisfactory | Constant | Fail | Good | No | Slow |
| 1A | 3.5 | 5 | Gelled | * | * | * | * | * |
| 1B | 3.5 | 23 | Satisfactory | Constant | Fail | Acceptable | No | Fast |

* = Not tested

TABLE 3

Evaluation Results with SMW Formulations - 5° C. and 23° C. Dosing Temperatures

| Batch Code | Gelatin Concn. % | Dosing Temp. ° C. | Dosability | Viscosity | Total Viable Count | Surface Appearance | Residue | Dispers. |
|---|---|---|---|---|---|---|---|---|
| 6A | 6.5 | 5 | Not Satis. | Variable | Pass | Acceptable | Little | Variable |
| 6B | 6.5 | 23 | Satisfactory | Constant | Fail | Acceptable | Little | Variable |
| 5A | 5.0 | 5 | Not Satis. | Variable | Pass | Acceptable | Some | Fast |
| 5B | 5.0 | 23 | * | * | * | * | * | * |
| 4A | 3.5 | 5 | Not Satis. | Variable | Pass | Poor | Some | Variable |
| 4B | 3.5 | 23 | Satisfactory | Very low | Fail | Acceptable | Little | Fast |

* = Not tested

Problems became apparent that seemed to be related to the selection of dosing temperature. As to exclusively high molecular weight formulations (HMW), seen in Table 2, dosed at a temperature of 5° C., all of the formulations containing exclusively high molecular weight gelatin gelled, making it impossible to conduct further assessment or to dose. At a dosing temperature of 23° C., all of the formulations containing exclusively high molecular weight gelatin failed the Total Viable Count; it seems that the high dosing temperature facilitated the growth of bacteria.

As to exclusively standard molecular weight formulations, seen in Table 3, at a dosing temperature of 5° C., all the formulations were unsatisfactory in dosing parameters. The viscosity was noted to initially increase, followed by a decrease with time. As with the exclusively high molecular weight formulations, all of the standard molecular weight formulations dosed at 23° C. failed the Total Viable Count, which resulted in the abandonment of testing before final data on Batch 5B. SMW formulations displayed generally variable dispersion times. Formulations displaying either "not satisfactory dosability" or "failing" the TVC were not tested for dispersion.

Due to the apparently temperature related poor performance of the formulations above, similar high and standard molecular weight formulations were evaluated with more intermediate formulation dosing temperatures; e.g., 10° C. and/or 15° C. Additionally, formulations comprising 4.0% and 3.0% w/w total high molecular weight gelatin concentration were tested, as were formulations comprising exclusively standard molecular weight gelatin at a concentration of 5.5%. At the same time, a limited test of balanced (50:50) formulations combining standard and high molecular weight formulations was undertaken. Formulations are seen in Table 4.

TABLE 4

High and Standard Molecular Weight Formulations; Intermediate Dosing Temperatures; Combined High and Standard Molecular Weight Formulations

| Batch Code | HMW Gelatin; % w/w | SMW Gelatin; % w/w | Mannitol % w/w | Dosing Temp. (° C.) |
|---|---|---|---|---|
| 3C | 6.5 | 0 | 5.5 | 10 |
| 3D | 6.5 | 0 | 5.5 | 15 |
| 12C | 5 | 0 | 2.96 | 10 |
| 17C | 3 | 0 | 2.54 | 10 |
| 22C | 4 | 0 | 3.38 | 10 |
| 6C | 0 | 6.5 | 5.5 | 10 |
| 6D | 0 | 6.5 | 5.5 | 15 |
| 16C | 0 | 5.5 | 4.65 | 10 |
| 11C | 0 | 5 | 2.96 | 10 |
| 7C | 3.25 | 3.25 | 5.5 | 10 |
| 7D | 3.25 | 3.25 | 5.5 | 15 |

TABLE 5

Evaluation Results with HMW Formulations - 10° C. and 15° C. Dosing Temperatures

| Gelatin Conc. % | ° C. | Dosability | Viscosity | Total Viable Count | Surface Appearance | Residue | Dispersion |
|---|---|---|---|---|---|---|---|
| 6.5 | 10 | Gelled | * | * | * | * | * |
| 6.5 | 15 | Satisfactory | Constant | Pass | Good | No/Little | Slow |
| 5.0 | 10 | Difficult | Variable | Pass | Good | No | Slow |
| 4.0 | 10 | Difficult | Increase with time | Pass | Acceptable | No | Variable |
| 3.0 | 10 | Difficult | Slight increase with time | Pass | Poor | No | Fast |

* = Not tested

Evaluation results, seen in Table 5, indicated a better performance than that seen at the 5° C. and 23° C. dosing temperatures (Tables 2 and 3), however, significant problems remained. At a dosing temperature of 10° C., the performance of the exclusively high molecular weight formulation remained problematic. The gelatin mix at that temperature showed the tendency to become more viscous with time. At 10° C. dosing temperature, the 6.5% total gelatin concentration formulation gelled and was therefore impossible to dose and evaluate. The remaining formulations, ranging from total gelatin concentrations of 3.0 to 5.0% (dosing temperature of 10° C.), were difficult to dose due to blockage of the dosing tube. A detailed description of viscosity measurements for HMW formulations is presented in Table 6.

For example, Batch 12C, a 5.0% total gelatin concentration formulation held at 10° C. showed an approximate tripling of viscosity from the initial time to the 34 hour hold point, followed by a return to near original viscosity levels at 49 hours. Batch 22C, a 4.0% total gelatin concentration held at 10° C., showed an approximate doubling of viscosity levels from the initial time to the maximum time, with no trend towards retrenchment to original levels. Such time dependent changes in viscosity may pose significant problems for commercial production, as the formulations may become too viscous to dose before it is possible to complete a commercially sized batch.

TABLE 6

HMW Formulations; Detailed Viscosity Assessment

| Gelatin Conc. % | Dosing Temp. °C. | Batch Code | Hold Time (hours) | Viscosity (mPas) @ Shear Rate (1/s) | | | | |
|---|---|---|---|---|---|---|---|---|
| | | | | 500 | 1000 | 1500 | 2000 | 2500 |
| 6.5 | 10 | 3C | | Not dosed as solution gelled | | | | |
| 6.5 | 15 | 3D | Initial | 16.0 | 15.1 | 14.6 | 14.4 | 14.6 |
| | | | 18 | 16.9 | 15.8 | 15.5 | 15.3 | 14.9 |
| | | | 24 | 17.7 | 17.1 | 16.9 | 16.5 | 16.2 |
| | | | 32 | 16.3 | 15.0 | 13.8 | 13.0 | — |
| | | | 43 | 17.6 | 16.5 | 16.6 | 15.9 | 15.8 |
| | | | 48 | 17.5 | 16.7 | 16.3 | 15.6 | 16.4 |
| 6.5 | 23 | 3B | Initial | 13.01 | 12.34 | 12.04 | 11.88 | 11.82 |
| | | | 23 | 14.31 | 13.14 | 13.44 | 12.73 | 12.65 |
| | | | 42 | Note 1 | Note 1 | Note 1 | Note 1 | Note 1 |
| 5.0 | 5 | 2A | | Not dosed as solution gelled | | | | |
| 5.0 | 10 | 12C | Initial | 10.0 | 10.1 | 9.4 | 9.6 | 9.2 |
| | | | 10 | 15.2 | — | — | — | — |
| | | | 19 | 11.0 | 10.8 | 10.2 | 10.3 | 10.3 |
| | | | 25 | 10.1 | 10.2 | 9.7 | 9.7 | 9.7 |
| | | | 34 | 34.2 | 29.6 | 27.3 | 26.3 | 24.6 |
| | | | 43 | 12.6 | 12.1 | 12.1 | 11.6 | 11.6 |
| | | | 49 | 11.1 | 10.9 | 10.9 | 10.5 | 10.4 |
| 5.0 | 23 | 2B | Initial | 7.47 | 7.16 | 7.75 | 7.09 | 7.31 |
| | | | 23 | 7.74 | 7.49 | 7.64 | 7.34 | 7.28 |
| | | | 42 | 6.81 | 7.07 | 6.86 | 7.31 | 7.28 |
| 4.0 | 10 | 22C | Initial | 9.2 | 8.8 | 9.4 | 8.8 | 8.8 |
| | | | 12 | 11.5 | 11.2 | 11.0 | 11.0 | 10.7 |
| | | | 25 | 14.3 | 13.3 | 12.6 | 12.4 | 12.1 |
| | | | 36 | 15.2 | 14.6 | 13.6 | 13.4 | 12.9 |
| | | | 49 | 18.9 | 17.7 | 16.8 | 15.8 | 15.0 |
| 3.5 | 5 | 1A | | Not dosed as solution gelled | | | | |
| 3.5 | 23 | 1B | Initial | 4.16 | 4.80 | 4.62 | 4.73 | 4.53 |
| | | | 23 | 4.51 | 4.46 | 4.78 | 4.51 | 4.70 |
| | | | 42 | 4.33 | 3.95 | 4.70 | 4.44 | 4.42 |
| 3.0 | 10 | 17C | Initial | 6.1 | 5.9 | 5.6 | 5.7 | 5.8 |
| | | | 18 | 6.6 | 7.0 | 6.6 | 6.5 | 6.7 |
| | | | 24 | 7.1 | 6.7 | 6.7 | 6.6 | 6.5 |
| | | | 41 | 8.9 | 8.5 | 8.5 | 8.2 | 8.2 |
| | | | 49 | 8.6 | 8.4 | 8.4 | 7.7 | 7.7 |

Note 1: Sample not tested due to computer problem for data acquisition.

In view of the fact that all batches held at 23° C. failed the Total Viable Count testing for bacterial growth, the only formulation displaying generally satisfactory dosing behavior was a formulation comprising 6.5% total gelatin concentration held at 15° C. (Batch 3D). While performance was acceptable for this formulation at 15° C., it was noted that this temperature represented a relatively small difference in the operating temperature from the experience at 23° C. of Experiment 1, in which similar formulations had failed the Total Viable Count. Therefore, utilization of this model on a production basis could represent processing temperatures that were unacceptably close to those promoting bacterial growth in the product. Additionally, this formulation (Batch 3D; 6.5% HMW gelatin held at 15° C.) was less than optimal in regards to other characteristics, in that it left minor residue in the packaging after removal and displayed both slow dispersion and slow disintegration.

On visual inspection, all of the formulations containing exclusively high molecular weight gelatin gave a product with a good white appearance. It was noted that surface appearance was good or acceptable for those units with higher levels of gelatin concentration, that is, above 4.0% w/w gelatin. As the concentration of gelatin was reduced, that is, at or below 4.0% w/w gelatin, the formulations were found to have more surface defects. Either no residue or a very little amount of residue remained in the packaging after product removal. At 3% w/w high molecular weight gelatin, the surface appearance is poor.

Because of the promise shown at 10° C. and 15° C. processing temperatures, a second round of experimentation was undertaken to refine the understanding of performance at various incremental temperature and gelatin concentration levels. Results were then data mapped according to the following protocol. Varying gelatin formulations were formulated and were assessed on five assessment criteria, detailed below, and scored on the basis of two points for good performance in each category, one point for acceptable performance in each category, and zero points for unacceptable performance in each category as seen in Table 7. Formulations were scored on the dosing and viscosity of the formulation, that is, qualities of dosing and viscosity of the formulation before freeze-drying and packaging; and on the appearance, strength, and dispersion of the finished fast dispersing dosage form. The scores were summed, with a zero in any category acting as a disqualifier, that is, reducing the score for the particular product to zero. Accordingly, fast dispersing dosage forms could have scores of 0, or 5-10, with five being the minimally acceptable score and 10 being an optimal score.

TABLE 7

Data Map Scoring System

| Description of Results | Score | Assessments on Formulation | |
|---|---|---|---|
| | | Dosing Performance | Viscosity |
| Good | 2 | Dosing the formulation without problem | Viscosity Stays Relatively Constant |
| Acceptable | 1 | Still dosable with some difficulties due to formulation becoming more viscous | Small change in viscosity (small gradual increase or decrease from initial) |
| Unsatisfactory | 0 | Not able to dose either because the formulation set into a gel or a semi-gel that became too difficult to dose. Splashing and dripping during dosing | Relatively noticeable increase or decrease in viscosity from initial |

| Description of Results | Score | Assessments on Finished Product | | |
|---|---|---|---|---|
| | | Appearance | Strength | Dispersion |
| Good | 2 | Good surface appearance without surface defects | Readily removable from the blister pocket with no residue of the units in the blister pockets | Dispersion in water in <10 sec. |
| Acceptable | 1 | Average surface appearance with some or few surface defects | Readily removable from the blister pocket with some or little residue in the blister pocket | Dispersion in water in <20 sec. |
| Unsatisfactory | 0 | Poor surface appearance with large number of surface defects | Fragile and break when removed from the blister pocket. Large amount of residue left in the blister pocket | Dispersion in water; >20 sec, or does not disperse |

The resulting scores were then data mapped in a tabular matrix, as seen in Table 8, in order to visually discern trends in formulation behavior. Actual measured parameters are shown in enlarged numerical type. Unmeasured data points falling between measured points were forecast based on performance of surrounding data points in the matrix; for example, in Table 8, when the gelatin formulations were dosed at 5° C., measured data points at gelatin concentrations of 3.5%, 5%, and 6.5% showed that the formulations all gelled, making dosing impractical. Therefore, similar gelling behavior is predicted for formulations with gelatin concentrations of 3%, 4%, 5.5%, and 6%.

In both actual and predicted experiments, for all formulations displaying a score of less than 10, that is, a less than optimal score, the assessment parameter causing the score reduction is identified in parentheses below the score.

Microbiological assessment, that is, Total Viable Count (TVC), was observed for each formulation but was not numerically calculated as part of the data mapping. As discussed above, all experiments were performed using standardized formulations without active ingredient. TVC's are suggestive only of results in actual production; since formulation compositions, pH, and possible additives, such as antibiotics or other biostatic additives, may affect resulting TVC. For example, a relatively warm processing temperature, such as the 23° C. levels used in this experiment, may cause unacceptable TVC results with certain formulations, but other formulations may be susceptible to additional components or manipulations that make processing at that temperature feasible.

TABLE 8

High Molecular Weight Gelatin (HMW)

| | | Gelatin Conc. % | | | | | | |
|---|---|---|---|---|---|---|---|---|
| | | 3 | 3.5 | 4 | 5 | 5.5 | 6 | 6.5 |
| 5° C. | | No data - Predict 0 (sol'n gelled) | 0 (Sol'n gelled) | No data - Predict 0 (sol'n gelled) | 0 (Sol'n gelled) | No data - Predict 0 (sol'n gelled) | No data - Predict 0 (sol'n gelled) | 0 (Sol'n gelled) |
| 10° C. | | 0 (appearance) | 9 (viscosity) | 0 (dosing) | 0 (dosing and dispersion) | No data - Predict 0 (dosing and dispersion) | No data - Predict 0 (sol'n gelled) | 0 (sol'n gelled) |
| 15° C. | | No data - Predict 0 (appearance) | No data - Predict 9 (viscosity) | No data - Predict 9 (dosing) | No data - Predict 0 (dispersion) | No data - Predict 0 (dispersion) | No data - Predict 0 (dispersion) | 0 (dispersion) |
| 23° C. | | No data - Predict 0 (appearance) | 10 | No data - Predict 10 | 0 (dispersion) | No data - Predict 0 (dispersion) | No data - Predict 0 (dispersion) | 0 (dispersion) |

The use of multifactorial assessment, with an unacceptable performance in any assessment area acting as a disqualifier, along with data mapping, exposed significant issues with the exclusively high molecular weight formulations. For example, while a formulation of 6.5% gelatin dosed at 15° C. exhibited acceptable dosing parameters in the earlier experiments (Tables 5 and 6); unacceptable dispersion time rendered it a commercially non-viable formulation.

In summary, for formulations containing only high molecular weight fish gelatin, maintaining a dosing temperature at 5° C. is not possible due to gelling of the formulation. In general, dosing at a temperature of 10° C. is possible but difficulties in dosing may be experienced at longer solution hold times due to a gradual increase in viscosity over time. Maintaining the dosing temperature above 10° C. provides acceptable dosing as the viscosity remains fairly constant. However, the microbiological quality of the solution is compromised if a dosing temperature above 15° C. is used, as seen in the samples held at 23° C. Additionally, the results indicate that the use of exclusively high molecular weight fish gelatin gave units with no or low levels of surface defects and no residue. As the HMW formulations with 4.0% or lower total gelatin concentrations, seen generally in the first four columns of the matrix of Table 8, had generally displayed fast dispersion and disintegration parameters (although they were difficult to dose at low temperature due to aeration of the mix in the dosing line), it was inferred that relatively higher concentrations of HMW gelatin contributes to poor dispersion and disintegration characteristics. In short, while it was possible to formulate an acceptable product utilizing only HMW gelatin, there were significant limitations and the product appeared most feasible for formulations comprising less than 5% w/w gelatin. Because of these limitations, evaluation was performed of formulations utilizing standard molecular weight (SMW) fish gelatin, in particular to evaluate the behavior of formulations having greater than 5% w/w SMW gelatin.

TABLE 9

Evaluation Results with SMW Formulations

| Gelatin Concn. % | Dosing Temp. ° C. | Dosability | Viscosity | Total Viable Count | Surface Appearance | Residue | Dispersion |
|---|---|---|---|---|---|---|---|
| 6.5 | 10 | Difficult. | Variable | Pass | Acceptable | Little | Variable |
| 6.5 | 15 | Satisfactory | Constant | Pass | Acceptable | Little | Variable |
| 5.5 | 10 | Satisfactory | Constant | Pass | Acceptable | No | Fast |
| 5.0 | 10 | Satisfactory | Constant | Pass | Acceptable | No | Fast |

TABLE 10

SMW Formulations; Detailed Viscosity Assessment

| Gelatin Conc. % | Dosing Temp. ° C. | Batch Code | Hold Time | Viscosity (mPas) @ Shear Rate (1/s) | | | | |
|---|---|---|---|---|---|---|---|---|
| | | | | 500 | 1000 | 1500 | 2000 | 2500 |
| 6.5 | 5 | 6A | Initial | 13.55 | 12.51 | 11.98 | 11.82 | 11.52 |
| | | | 23 | 23.67 | 21.38 | 20.20 | 19.51 | 19.06 |
| | | | 42 | 12.69 | 11.60 | 11.72 | 11.17 | 10.79 |
| 6.5 | 10 | 6C | Initial | 7.7 | 8.0 | 7.7 | 7.6 | 7.8 |
| | | | 18 | 8.4 | 8.7 | 8.1 | 8.5 | 8.2 |
| | | | 24 | 8.3 | 8.3 | 8.5 | 8.0 | 7.9 |
| | | | 32 | 11.7 | 10.7 | 10.9 | 10.3 | 10.3 |
| | | | 43 | 13.3 | 12.4 | 12.6 | 12.1 | 11.9 |
| | | | 48 | 8.2 | 8.4 | 7.9 | 8.2 | 8.1 |
| 6.5 | 15 | 6D | Initial | 7.6 | 7.3 | 7.3 | 6.9 | 6.7 |
| | | | 18 | — | — | — | — | — |
| | | | 24 | 7.7 | 7.2 | 6.7 | 7.0 | 6.9 |
| | | | 32 | 7.2 | 7.0 | 6.9 | 6.8 | 6.9 |
| | | | 43 | 7.3 | 7.1 | 6.8 | 7.0 | 7.0 |
| | | | 48 | 7.4 | 7.3 | 7.1 | 7.1 | 6.7 |
| 6.5 | 23 | 6B | Initial | 5.83 | 5.56 | 5.64 | 5.77 | 5.84 |
| | | | 23 | 6.08 | 5.86 | 5.23 | 5.81 | 5.51 |
| | | | 48 | — | — | — | — | — |
| 5.5 | 10 | 16C | Initial | 6.5 | 6.3 | 6.1 | 6.3 | 6.4 |
| | | | 18 | 6.2 | 6.8 | 6.5 | 6.6 | 6.7 |
| | | | 24 | 6.4 | 6.3 | 6.5 | 6.5 | 6.8 |
| | | | 41 | 6.9 | 6.9 | 6.8 | 6.9 | 6.7 |
| | | | 49 | 6.6 | 7.0 | 6.4 | 6.6 | 6.8 |
| 5.0 | 5 | 5A | Initial | 6.71 | 7.13 | 7.49 | 7.07 | 7.21 |
| | | | 23 | 17.73 | 16.36 | 15.58 | 14.97 | 14.70 |
| | | | 42 | 8.29 | 7.44 | 7.72 | 7.10 | 7.02 |
| 5.0 | 10 | 11C | Initial | 5.4 | 5.1 | 5.3 | 5.2 | 5.3 |
| | | | 10 | 4.3 | Note 1 | Note 1 | Note 1 | Note 1 |
| | | | 19 | 4.3 | 4.9 | 4.9 | 5.0 | 4.7 |
| | | | 25 | 4.9 | 5.0 | 4.8 | 5.0 | 5.0 |
| | | | 34 | 6.9 | 6.1 | 5.5 | 5.7 | 5.7 |
| | | | 43 | 4.6 | 5.1 | 5.2 | 5.0 | 5.3 |
| | | | 49 | 4.7 | 5.1 | 4.8 | 5.3 | 5.1 |
| 3.5 | 5 | 4A | Initial | 4.90 | 4.37 | 5.11 | 4.36 | 4.76 |
| | | | 23 | 7.56 | 7.26 | 7.51 | 7.11 | 6.97 |
| | | | 48 | 5.02 | 4.64 | 4.95 | 4.41 | 4.52 |

Note 1: Sample not tested due to computer problem for data acquisition.

As to formulations containing only standard molecular weight gelatin, seen in Tables 9 and 10, formulations containing more than 5.5% gelatin often displayed difficulty in dosing due to aeration of mix at low temperature, while the 6.5% gelatin concentration dosed at 15° C. displayed satisfactory dosing parameters but variable dispersion. Formulations with higher gelatin content (6.5%) had better surface appearance, but tended to have variable dispersion times. On the other hand, formulations with 5.5% or less total SMW gelatin had more surface defects, but fast dispersion. Batch 16C displayed good viscosity characteristics, but displayed somewhat poor surface appearance, as did Batch 11C.

As with the previous experiment using exclusively high molecular weight formulations, a round of experiments was conducted using exclusively standard molecular weight gelatin, and utilizing the same multifactorial assessment scale and data mapping as the previous HMW experiment. Results are seen in Table 11.

TABLE 11

Standard Molecular Weight Gelatin (SMW)

| | | Gelatin Conc. % | | | | | |
|---|---|---|---|---|---|---|---|
| | 3 | 3.5 | 4 | 5 | 5.5 | 6 | 6.5 |
| 5° C. | No data - Predict 0 (dosing, appearance) | 0 (dosing, appearance) | No data - Predict 0 (dosing) | 0 (dosing, viscosity) | No data - Predict 0 (dosing, viscosity) | No data - Predict 0 (dosing, viscosity) | 0 (dosing, viscosity, dispersion) |
| 10° C. | No data - Predict 0 (dosing, appearance) | 0 (appearance) | 0 (appearance) | 9 (appearance) | 9 (appearance) | 9 (appearance) | 0 (dispersion) |
| 15° C. | No data - Predict 0 (appearance) | No data - Predict 0 (appearance) | No data - Predict 0 (appearance) | No data - Predict 9 (appearance) | No data - Predict 9 (appearance) | No data - Predict 9 (appearance) | 0 (dispersion) |
| 23° C. | No data - Predict 0 (appearance) | 0 (appearance) | No data - Predict 0 (appearance) | No data - Predict 9 (appearance) | No data - Predict 9 (appearance) | No data - Predict 9 (appearance) | 0 (dispersion) |

As noted, as an adjunct to the HMW/SMW studies detailed above, limited experimentation was undertaken with an equal mix of high and standard molecular weight gelatin, to a total of 6.5% total gelatin concentration. Surprisingly, as seen in Table 12, this mixture showed promise, displaying good dosing and viscosity parameters, few surface defects and little packaging residue, but having slow dispersion behavior. Accordingly, experimentation was expanded using variable ratios of high and standard molecular weight fish gelatin at varying dosing temperatures, as seen in Table 13.

TABLE 12

Evaluation Results with Combined HMW and SMW Formulations-
10° C. and 15° C. Dosing Temperatures

| Gelatin Ratio. HMW:SMW | ° C. | Dosability | Viscosity | Total Viable Count | Surface Appearance | Residue | Dispers. |
|---|---|---|---|---|---|---|---|
| 3.25/3.25 | 10 | Gelled | * | * | * | * | * |
| 3.25/3.25 | 15 | Satisfactory | Constant | Pass | Good | Little | Slow |

* = Not tested

TABLE 13

Evaluation Results with Combined HMW and SMW Formulations;
6.5%-5.0% Total Gelatin; Varying HMW:SMW Ratio

| Gelatin Conc. % | Dosing Temp ° C.; Ratio HMW:SMW | Dosability | Viscosity | Total Viable Count | Surface Appearance | Residue | Dispersion |
|---|---|---|---|---|---|---|---|
| 6.5 | 15° 50:50 | Satis. | Constant | Pass | Few | Little | Slow |
| 6.5 | 10° 50:50 | Gelled | * | * | * | * | * |
| 6.5 | 10° 10:90 | Satis. | Slight increase then decrease with time | Pass | Some | No | Fast |

TABLE 13-continued

Evaluation Results with Combined HMW and SMW Formulations;
6.5%-5.0% Total Gelatin; Varying HMW:SMW Ratio

| Gelatin Conc. % | Dosing Temp ° C.; Ratio HMW:SMW | Dosability | Viscosity | Total Viable Count | Surface Appearance | Residue | Dispersion |
|---|---|---|---|---|---|---|---|
| 6.5 | 10° 5:95 | Satis | Slight increase then decrease with time | Pass | Some | No | Fast |
| 6.5 | 10° 3:97 | Satis. | Slight increase then decrease with time | Pass | Some | Little | Fast |
| 5.5 | 10° 25:75 | Satis. Start, unsatis. At 48 hours | Slight increase with time | Pass | No/Few Bubbles | No | Variable |
| 5.0 | 10° 50:50 | Satisfactory at start, unsatis. At 48 hours | Increase and decrease with time | Pass | No | No | Variable |
| 5.0 | 10° 35:65 | Satisfactory at start, unsatis. At 48 hours | Slow increase with time | Pass | No | No | Variable |
| 5.0 | 10° 25:75 | Satis. | Slight increase then decrease with time | Pass | No | No | Fast |
| 5.0 | 10° 10:90 | Satis. | Slight increase with time | Pass | No | No | Fast |

\* = Not tested

As seen in Table 13, excellent results were obtained by varying the total fish gelatin concentration and altering the ratio of high molecular weight to standard molecular weight fish gelatin as a dependent variable. The dosability and consistency in viscosity throughout the dosing period is dependant on the total gelatin concentration and the ratio of HMW:SMW fish gelatin present in the formulation. At higher total gelatin concentration and for those with a higher proportion of HMW fish gelatin, the formation tends to gel or present poor dispersion. By reducing, for example, the level of gelatin in the combination and selecting the appropriate ratio of HMW:SMW fish gelatin, satisfactory dosing and acceptable solution viscosity could be achieved.

Microbiological quality assessment showed that TVC of less than 10 cfu/ml were generally reported when the solution was held at either 10° C. or 15° C. However, due to the earlier experience (see, e.g., Tables 2 and 3), with multiple batches failing the TVC when held at 23° C., and given that satisfactory results were obtained with dosing temperatures of 10° C., most experimentation was concentrated at that temperature (10° C.). However, experimentation clearly showed that higher dosing temperatures are feasible, if microbial growth issues can be overcome.

In terms of visual appearance, all of the dosed units gave a light cream color in appearance. It was noted that no, or only rare, surface defects were found in the individually dosed units, except for those formulations with a low proportion of HMW fish gelatin. Little or no residue remained in the packaging after the removal of any of the units.

As to dispersion, the dosed units having a higher level of fish gelatin concentration (e.g., 6.5% w/w gelatin) and a higher proportion of HMW fish gelatin (e.g., HMW:SMW ratio of 50:50) showed slow or variable dispersion times. The dispersion improved for formulations with lower fish gelatin concentration (e.g., 5.0% w/w fish gelatin) and a lower proportion of HMW fish gelatin (e.g., HMW:SMW ratio of 10:90).

Accordingly, multifactorial assessment and data mapping were used, according to the protocol set out above. Formulations were evaluated at dosing temperatures of 5° C., 10° C., 15° C. and 23° C. Gelatin formulations containing 3%, 3.5%, 4%, 5%, 5.5%, 6%, and 6.5% w/w fish gelatin were assessed in fast dispersing dosage forms wherein the total gelatin represented a ratio of 50:50 HMW/SMW gelatin, 35:65 HMW/SMW gelatin, 25:75 HMW/SMW gelatin, and 10:90 HMW/SMW gelatin. Results are seen in Tables 14 though 17.

TABLE 14

50:50 w/w Ratio of HMW:SMW Gelatin

| Dosing Temp. | Gelatin Conc. % | | | | | | |
|---|---|---|---|---|---|---|---|
| | 3 | 3.5 | 4 | 5 | 5.5 | 6 | 6.5 |
| 5° C. | No data - Predict 0 (sol'n gelled) | No data - Predict 0 (sol'n gelled) | No data - Predict 0 (sol'n gelled) | No data - Predict 0 (sol'n gelled) | No data - Predict 0 (sol'n gelled) | No data - Predict 0 (sol'n gelled) | No data - Predict 0 (sol'n gelled) |

TABLE 14-continued

50:50 w/w Ratio of HMW:SMW Gelatin

| Dosing Temp. | Gelatin Conc. % | | | | | | |
|---|---|---|---|---|---|---|---|
| | 3 | 3.5 | 4 | 5 | 5.5 | 6 | 6.5 |
| 10° C. | No data - Predict 0 (appearance) | 8 (viscosity, appearance) | 9 (viscosity) | 0 (dispersion) | No data - Predict 0 (dosing, dispersion) | No data - Predict 0 (dosing, dispersion) | 0 (sol'n gelled) |
| 15° C. | No data - Predict 0 (appearance) | No data - Predict 8 (viscosity, appearance) | No data - Predict 9 (viscosity) | No data - Predict 0 (dispersion) | No data - Predict 0 (dispersion) | No data - Predict 0 (dispersion) | 0 (dispersion) |
| 23° C. | No data - Predict 0 (appearance) | No data - Predict 9 (appearance) | No data - Predict 10 | No data - Predict 0 (dispersion) | No data - Predict 0 (dispersion) | No data - Predict 0 (dispersion) | No data - Predict 0 (dispersion) |

TABLE 15

35:65 w/w Ratio of HMW:SMW Gelatin

| Dosing Temp. | Gelatin Conc. % | | | | | | |
|---|---|---|---|---|---|---|---|
| | 3 | 3.5 | 4 | 5 | 5.5 | 6 | 6.5 |
| 5° C. | No data - Predict 0 (sol'n gelled or dosing) | No data - Predict 0 (sol'n gelled or dosing) | No data - Predict 0 (sol'n gelled or dosing) | No data - Predict 0 (sol'n gelled or dosing) | No data - Predict 0 (sol'n gelled or dosing) | No data - Predict 0 (sol'n gelled or dosing) | No data - Predict 0 (sol'n gelled or dosing) |
| 10° C. | No data - Predict 0 (appearance) | No data - Predict 8 (viscosity, appearance) | 9 (viscosity) | 8 (dosing, viscosity) | No data - Predict 8 (dosing, dispersion) | No data - Predict 8 (dosing, dispersion) | No data - Predict 0 (sol'n gelled or dispersion) |
| 15° C. | No data - Predict 0 (appearance) | No data - Predict 8 (viscosity, appearance) | No data - Predict 9 (viscosity) | No data - Predict 8 (dosing, viscosity) | No data - Predict 8 (dosing, dispersion) | No data - Predict 8 (dosing, dispersion) | No data - Predict 0 (dispersion) |
| 23° C. | No data - Predict 0 (appearance) | No data - Predict 9 (appearance) | No data - Predict 10 | No data - Predict 10 | No data - Predict 9 (, dispersion) | No data - Predict 9 (dispersion) | No data - Predict 0 (dispersion) |

TABLE 16

25:75 w/w Ratio of HMW:SMW Gelatin

| Dosing Temp. | Gelatin Conc. % | | | | | | |
|---|---|---|---|---|---|---|---|
| | 3 | 3.5 | 4 | 5 | 5.5 | 6 | 6.5 |
| 5° C. | No data - Predict 0 (sol'n gelled, or dosing) | No data - Predict 0 (sol'n gelled or dosing) | No data - Predict 0 (sol'n gelled or dosing) | No data - Predict 0 (sol'n gelled or dosing) | No data - Predict 0 (sol'n gelled or dosing) | No data - Predict 0 (sol'n gelled or dosing) | No data - Predict 0 (sol'n gelled or dosing) |

TABLE 16-continued

25:75 w/w Ratio of HMW:SMW Gelatin

| Dosing Temp. | Gelatin Conc. % | | | | | | |
|---|---|---|---|---|---|---|---|
| | 3 | 3.5 | 4 | 5 | 5.5 | 6 | 6.5 |
| 10° C. | No data - Predict 0 (appearance) | 9 (appearance) | 10 | 10 | 9 (dispersion) | No data - Predict 9 (appearance) | No data - Predict 0 (sol'n gelled or dispersion) |
| 15° C. | No data - Predict 0 (appearance) | No data - Predict 9 (appearance) | No data - Predict 10 | No data - Predict 10 | No data - Predict 9 (dispersion) | No data - Predict 9 (dispersion) | No data - Predict 0 (dispersion) |
| 23° C. | No data - Predict 0 (appearance) | No data - Predict 9 (appearance) | No data - Predict 10 | No data - Predict 10 | No data - Predict 9 (dispersion) | No data - Predict 9 (dispersion) | No data - Predict 0 (dispersion) |

TABLE 17

10:90 w/w Ratio of HMW:SMW Gelatin

| Dosing Temp | Gelatin Conc. % | | | | | | |
|---|---|---|---|---|---|---|---|
| | 3 | 3.5 | 4 | 5 | 5.5 | 6 | 6.5 |
| 5° C. | No data - Predict 0 (dosing) | No data - Predict 0 (dosing) | No data - Predict 0 (dosing, viscosity) | No data - Predict 0 (dosing, viscosity) | No data - Predict 0 (dosing, viscosity) | No data - Predict 0 (dosing, viscosity) | No data - Predict 0 (dosing, viscosity, dispersion) |
| 10° C. | No data - Predict 0 (appearance) | 0 (appearance) | 10 | 10 | 10 | 10 | 0 (dispersion) |
| 15° C. | No data - Predict 0 (appearance) | No data - Predict 0 (appearance) | No data - Predict 10 | No data - Predict 10 | No data - Predict 10 | 10 | No data - Predict 0 (dispersion) |
| 23° C. | No data - Predict 0 (appearance) | No data - Predict 0 (appearance) | No data - Predict 10 | No data - Predict 10 | No data - Predict 10 | No data - Predict 10 | No data - Predict 0 (dispersion) |

When summarized, the data mapping revealed three general areas of compositional performance, as seen in Table 18, in which three generally acceptable areas of performance can be more easily seen. In the upper left most area of Table 18, it can be seen that formulations with relatively high proportions of HMW performed well. In the bottom right-most area of Table 18, it can be seen that formulations with relatively low proportions of HMW gelatin performed well. Across the center of Table 18, it can be seen that formulations in which the ratio of HMW:SMW gelatin was about 35:65 and 25:75 performed best across the widest range of gelatin concentrations.

TABLE 18

Summary of Data Mapping by HMW:SMW Ratio and Gelatin Concentration (%)

| Ratio of HMW:SMW | Total Gelatin Concentration (w/w) | | | | | | |
|---|---|---|---|---|---|---|---|
| | 3% | 3.5% | 4% | 5% | 5.5% | 6% | 6.5% |
| 100:0 | 0 | 9 | 0 | 0 | 0* | 0* | 0 |
| 50:50 | 0* | 8 | 9 | 0 | 0* | 0* | 0 |
| 35:65 | 0* | 8* | 9 | 8 | 8* | 8* | 0* |
| 25:75 | 0* | 9 | 10 | 10 | 9 | 9* | 0* |
| 10:90 | 0* | 0 | 10 | 10 | 10 | 10 | 0 |
| 0:100 | 0* | 0 | 0 | 9 | 9 | 9 | 0 |

*Data Predicted

The general trend of Table 18 is more easily discerned if the same information is broken out as three separate functional areas, presented in Tables 19 through 21. Formulations in which HMW gelatin ranges up to approximately 50% w/w of the composition function best in those formulations in which the total gelatin concentration is approximately 3.5% to 4%.

TABLE 19

Performance When HMW Gelatin Comprises Approximately 50% or more of Formulation (Upper-most area of Table 18)

| Ratio of | Total Gelatin Concentration (w/w) | | | | | | |
|---|---|---|---|---|---|---|---|
| HMW:SMW | 3% | 3.5% | 4% | 5% | 5.5% | 6% | 6.5% |
| 100:0 | 0 | 9 | 0 | 0 | 0* | 0* | 0 |
| 50:50 | 0* | 8 | 9 | 0 | 0* | 0* | 0 |

*Data Predicted

A formulation in which the HMW:SMW gelatin ratio lies in the area of approximately 35:65 and 25:75 functions well over a wide range of total gelatin concentrations, that is, from approximately 3.5% to 6%.

TABLE 20

Performance When HMW:SMW Ratio is Approximately 35:65 or more of Formulation (Central band across Table 18)

| Ratio of | Total Gelatin Concentration (w/w) | | | | | | |
|---|---|---|---|---|---|---|---|
| HMW:SMW | 3% | 3.5% | 4% | 5% | 5.5% | 6% | 6.5% |
| 35:65 | 0* | 9* | 9 | 8 | 8* | 8* | 0* |

*Data Predicted

Finally, formulations in which the HMW:SWM gelatin ratio is higher than approximately 25:75, with SMW gelatin predominating, functions well at total gelatin concentrations of approximately 4% to 6%.

TABLE 21

Performance When HMW:SMW Ratio is Approximately 25:75 or less of Formulation (Bottom-most area of Table 18)

| Ratio of | Total Gelatin Concentration (w/w) | | | | | | |
|---|---|---|---|---|---|---|---|
| HMW:SMW | 3% | 3.5% | 4% | 5% | 5.5% | 6% | 6.5% |
| 25:75 | 0* | 9 | 10 | 10 | 9 | 9* | 0* |
| 10:90 | 0* | 0 | 10 | 10 | 10 | 10 | 0 |
| 0:100 | 0* | 0 | 0 | 9 | 9 | 9 | 0 |

*Data Predicted

CONCLUSION

The formulation development and optimization of the instant invention evaluated three options using fish gelatin. These were (1) use of HMW fish gelatin alone, (2) use of SMW fish gelatin alone and (3) use of a combination HMW and SMW fish gelatin.

Use of high molecular weight gelatin alone in formulations tends to give units with good surface appearance, but tends to cause gelling or to become more viscous at low dosing temperature. Although this can be overcome by higher dosing temperatures, the microbiological quality of the formulation is compromised at higher dosing temperatures. Alternatively, the tendency to increased viscosity may be overcome by reducing the concentration of gelatin in the formulation, but this resulted in a unit with poor surface appearance due to the presence of surface defects. In addition, HMW formulations tend to give slow dispersing tablets. Exclusively HMW gelatin was most suitable for formulations with relatively low total concentrations of fish gelatin.

Exclusively SMW formulations tend to give units with poor surface appearance in terms of surface defects except when the formulation contains a higher concentration of fish gelatin. However, the viscosity is not constant over time which influences the dosing performance. The dispersion performance is also generally faster using only SMW gelatin. Exclusively SMW gelatin was most suitable for formulations with relatively high concentrations of gelatin.

Accordingly, a strategy is demonstrated for designing gelatin carrier compositions for fast dispersing dosage forms that may require certain gelatin concentrations. For example, in a fast dispersing dosage form in which the active ingredient may best be formulated using a relatively low gelatin concentration in the carrier, compositions may be empirically predicted and designed to optimize the use of HMW gelatin. Conversely, in fast dispersing dosage forms where a relatively high gelatin concentration may be desired or required, a composition may be tailored based on a higher percentage of SMW gelatin.

With the HMW/SMW combination formulation, when using an appropriate concentration of gelatin and an appropriate ratio of HMW:SMW, a formulation with good dosing performance and acceptable viscosity can be achieved. Finished product with acceptable surface appearance and fast dispersion can also be obtained. In sum, for optimal performance, gelatin concentration is to be directly varied according to the relative concentration of SMW gelatin in the overall formulation; and inversely varied according to the relative concentration of HMW gelatin in the overall formulation.

The composition according to the invention can also contain, in addition to the active ingredient or ingredients and fish gelatin carrier, other matrix forming agents and secondary components. By way of example and not limitation, other active ingredients, agents, and components may include those listed in U.S. Pat. No. 6,709,669, incorporated herein by reference.

For example, a clinically effective amount of Fentanyl (N-phenyl-N-[1-(2-phenylethyl)-4-piperidinyl] propanamide), is added to a 35:65 HMW/SMW gelatin carrier pre-mix of the above protocol. The formulation displays acceptable dosability and viscosity during a 48-hour hold period. The formulation is dosed into discrete units, frozen, and then freeze-dried. The units display acceptable appearance, strength, and dispersion times. As a further example, a clinically effective amount of apomorphine hydrochloride is added to a 35:65 HMW/SMW gelatin carrier pre-mix of the above protocol. The formulation displays acceptable dosability and viscosity during a 48-hour hold period. The formulation is dosed into discrete units, frozen, and then freeze-dried. The units display acceptable appearance, strength, and dispersion times. As yet another example, a clinically effective amount of dextromethorphan HBr, a purified hydrogenated phosphatidylcholine of soybean origin comprising at least 98 percent phosphatidylcholine, and aspartame as a sweetener is added to a 35:65 HMW/SMW gelatin carrier pre-mix of the above protocol. The formulation displays acceptable dosability and viscosity during a 48-hour hold period. The formulation is dosed into discrete units, frozen, and then freeze-dried. The units display acceptable appearance, strength, and dispersion times.

The precise quantity of active ingredient will vary according to the particular drug selected and the patient's needs.

However, the active ingredient can be generally present in an amount from about 0.01% to about 85%, typically from about 0.2% to about 60%, by weight of the dried dosage form.

The detailed description set forth above is intended merely as a description of the presently preferred embodiments of the invention, and is not intended to represent the only form in which the present invention may be formulated or utilized.

INDUSTRIAL APPLICABILITY

The pharmaceutical industry has utilized fish gelatin for the creation of readily dispersing formulations in which the fish gelatin either encapsulates at least one active ingredient, or acts as a carrier matrix for one, or a plurality, of such ingredients. The present method and formulation provides a fast dispersing dosage form in which at least one fish gelatin, selected on the basis of the gelatin's molecular weight profile, may be predetermined, among other factors, based on the predicted final gelatin concentration of the carrier.

The invention has been described with reference to various specific and preferred embodiments and techniques. However, it should be understood that many variations and modifications can be made while remaining within the spirit and scope of the invention.

We claim:

1. A process for preparing a pharmaceutical composition in a fast dispersing dosage form containing at least one active ingredient and at least one carrier comprising the steps of:
   selecting the at least one carrier based at least in part on the molecular weight profile of the carrier and a predetermined final total gelatin concentration between 3.5% and 6.0% w/w of the composition,
   wherein the at least one carrier is inert to the active ingredient and wherein the at least one carrier is a combination of high molecular weight fish gelatin and standard molecular weight fish gelatin, and
   wherein the ratio of high molecular weight fish gelatin to standard molecular weight fish gelatin is 50:50 to 10:90;
   forming a mixture of the at least one active ingredient and the at least one carrier in a suitable solvent to create a formulation;
   cooling the formulation to an intermediate formulation dosing temperature;
   dosing the formulation into discrete units at the intermediate formulation dosing temperature;
   solidifying the discrete units; and
   removing the solvent from the solid discrete units to form a network of the at least one active ingredient and the at least one carrier;
   wherein the formulation has a total viable count of less than 1000 cfu/ml;
   wherein the solid discrete units have an acceptable surface appearance;
   wherein the formulation exhibits a fairly constant viscosity over a period of about 48 hours; and
   wherein the high molecular weight fish gelatin is a fish gelatin in which more than 50% of the molecular weight distribution is greater than 30,000 daltons and the standard molecular weight fish gelatin is a fish gelatin in which more than 50% of the molecular weight distribution is below 30,000 daltons.

2. The process according to claim 1, wherein the fish gelatin is a non-gelling fish gelatin at room temperature.

3. The process according to claim 1, wherein the fish gelatin is non-hydrolyzed.

4. The process according to claim 1, wherein the solvent is water.

5. The process according to claim 1, wherein the solvent is removed from the discrete units by freeze-drying.

6. The process according to claim 1, wherein the solvent is removed from the discrete units by forced-air drying.

7. The process according to claim 1, wherein the solvent is removed from the discrete units by a second solvent removal process.

8. The process according to claim 1, wherein the high molecular weight fish gelatin is a fish gelatin in which more than 60% of the molecular weight distribution is greater than 30,000 daltons.

9. The process according to claim 1, wherein the high molecular weight fish gelatin is a fish gelatin in which more than 70% of the molecular weight distribution is greater than 30,000 daltons.

10. The process according to claim 1, wherein the standard molecular weight fish gelatin is a fish gelatin in which more than 60% of the molecular weight distribution is below 30,000 daltons.

11. The process according to claim 1, wherein the standard molecular weight fish gelatin is a fish gelatin in which more than 70% of the molecular weight distribution is below 30,000 daltons.

12. The process according to claim 1, wherein the combination of high molecular weight and standard molecular weight gelatin contains more than 50% w/w high molecular weight gelatin.

13. The process according to claim 8, wherein the combination of high molecular weight and standard molecular weight gelatin contains more than 50% w/w standard molecular weight gelatin.

14. The process according to claim 1, wherein the combination of high molecular weight and standard molecular weight gelatin contains high molecular weight gelatin and standard molecular weight gelatin in substantially the w/w ratio 1:1.

15. The process according to claim 1, wherein the combination of high molecular weight and standard molecular weight gelatin contains high molecular weight gelatin and standard molecular weight gelatin in substantially the w/w ratio 1:2.

16. The process according to claim 1, wherein the combination of high molecular weight and standard molecular weight gelatin contains high molecular weight gelatin and standard molecular weight gelatin in substantially the w/w ratio 1:3.

17. The process according to claim 1, wherein the combination of high molecular weight and standard molecular weight gelatin contains high molecular weight gelatin and standard molecular weight gelatin in substantially the w/w ratio 1:9.

18. The process according to claim 1, wherein the composition is designed for oral administration and releases the active ingredient rapidly in the oral cavity.

19. The process according to claim 1, wherein the composition disperses within 1 to 30 seconds of being placed in contact with fluid.

20. The process according to claim 1, wherein the composition disperses within 1 to 20 seconds of being placed in contact with fluid.

21. The process according to claim 1, wherein the composition disperses within 1 to 10 seconds of being placed in contact with fluid.

22. A solid, oral, rapidly disintegrating dosage form of a pharmaceutically active substance prepared by a process according to claim 13, which may also contain at least one additional ingredient selected from the group consisting of coloring agents, flavoring agents, excipients, and multiple therapeutic agents.

23. A solid, oral, rapidly disintegrating dosage form of a pharmaceutically active substance prepared by a process according to claim 1.

24. A solid, oral, rapidly disintegrating dosage form of a pharmaceutically active substance prepared by a process according to claim 8.

25. A solid, oral, rapidly disintegrating dosage form of a pharmaceutically active substance prepared by a process according to claim 9.

26. A solid, oral, rapidly disintegrating dosage form of a pharmaceutically active substance prepared by a process according to claim 10.

27. A solid, oral, rapidly disintegrating dosage form of a pharmaceutically active substance prepared by a process according to claim 11.

28. A solid, oral, rapidly disintegrating dosage form of a pharmaceutically active substance prepared by a process according to claim 12.

29. A solid, oral, rapidly disintegrating dosage form of a pharmaceutically active substance prepared by a process according to claim 13.

30. A solid, oral rapidly disintegrating dosage form of a pharmaceutically active substance prepared by a process according to claim 14.

31. A solid, oral rapidly disintegrating dosage form of a pharmaceutically active substance prepared by a process according to claim 15.

32. A solid, oral rapidly disintegrating dosage form of a pharmaceutically active substance prepared by a process according to claim 16.

33. A solid, oral rapidly disintegrating dosage form of a pharmaceutically active substance prepared by a process according to claim 17.

* * * * *